United States Patent
Jia et al.

(10) Patent No.: US 9,984,464 B2
(45) Date of Patent: May 29, 2018

(54) SYSTEMS AND METHODS OF CHOROIDAL NEOVASCULARIZATION DETECTION USING OPTICAL COHERENCE TOMOGRAPHY ANGIOGRAPHY

(71) Applicant: Oregon Health & Science University, Portland, OR (US)

(72) Inventors: Yali Jia, Portland, OR (US); David Huang, Portland, OR (US); Li Liu, Portland, OR (US)

(73) Assignee: Oregon Health & Science University, Portland, OR (US)

(*) Notice: Subject to any disclaimer, the term of this patent is extended or adjusted under 35 U.S.C. 154(b) by 0 days. days.

(21) Appl. No.: 15/721,070

(22) Filed: Sep. 29, 2017

(65) Prior Publication Data

US 2018/0025495 A1  Jan. 25, 2018

Related U.S. Application Data

(63) Continuation of application No. 15/080,498, filed on Mar. 24, 2016, now abandoned.

(60) Provisional application No. 62/138,196, filed on Mar. 25, 2015, provisional application No. 62/196,802, filed on Jul. 24, 2015.

(51) Int. Cl.
| | |
|---|---|
| *G06K 9/00* | (2006.01) |
| *G06T 7/00* | (2017.01) |
| *A61B 3/10* | (2006.01) |
| *G06T 7/136* | (2017.01) |
| *G01B 9/02* | (2006.01) |

(52) U.S. Cl.
CPC ............ *G06T 7/0016* (2013.01); *A61B 3/102* (2013.01); *G01B 9/02091* (2013.01); *G06T 7/136* (2017.01); *G06T 2207/10101* (2013.01); *G06T 2207/20036* (2013.01); *G06T 2207/20192* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 2011/0275931 A1* | 11/2011 | Debuc | A61B 3/102 600/425 |
| 2014/0073917 A1* | 3/2014 | Huang | A61B 5/0066 600/427 |
| 2016/0174830 A1* | 6/2016 | Rubin | A61B 3/102 351/206 |
| 2016/0227999 A1* | 8/2016 | An | A61B 3/1233 |
| 2017/0035286 A1* | 2/2017 | Meyer | A61B 3/102 |
| 2017/0169565 A1* | 6/2017 | Huang | G06T 7/0012 |

OTHER PUBLICATIONS

Zhang et al. ("Minimizing projection artifacts for accurate presentation of choroidal neovascularization in OCT micro-angiography", 2015).*

* cited by examiner

*Primary Examiner* — Avinash Yentrapati
(74) *Attorney, Agent, or Firm* — Schwabe, Williamson & Wyatt, P.C.

(57) ABSTRACT

Disclosed are systems and methods to automatically detect choroidal neovascularization (CNV) in the outer retina using OCT angiography. Further disclosed are methods of removing projection artifacts from the outer retina and for combining brightness, orientation, and position information in a context-aware saliency model to quantify CNV area in OCT angiograms.

32 Claims, 7 Drawing Sheets

SYSTEMS AND METHODS OF CHOROIDAL NEOVASCULARIZATION DETECTION USING OPTICAL COHERENCE TOMOGRAPHY ANGIOGRAPHY

CROSS REFERENCE TO RELATED APPLICATIONS

The present application is a Continuation Application of U.S. application Ser. No. 15/080,498, filed Mar. 24, 2016, entitled "SYSTEM AND METHODS OF CHOROIDAL NEOVASCULARIZATION DETECTION USING OPTICAL COHERENCE TOMOGRAPHY ANGIOGRAPHY," which claims priority to U.S. Provisional Patent Application No. 62/138,196 filed Mar. 25, 2015 and U.S. Provisional Patent Application No. 62/196,802 filed Jul. 24, 2015, all of which are hereby incorporated by reference.

ACKNOWLEDGEMENT OF GOVERNMENT SUPPORT

This invention was made with the support of the United States government under the terms of Grant Number R01 EY024544 awarded by the National Institutes of Health. The United States government has certain rights in this invention.

FIELD

Generally, the field involves methods of using optical coherence tomography (OCT) in angiography. More specifically, the field involves methods of processing OCT angiography images to detect and characterize choroidal neovascularization.

BACKGROUND

Age-related macular degeneration (AMD) is the leading cause of blindness in people 50 years or older in the developed world (Pascolini D et al, *Ophthalmic Epidemiol* 11, 67-115 (2004) and Jaeger R et al, *N Engl J Med* 358, 2602-2617 (2008); both of which are incorporated by reference herein). The advanced, neovascular form of AMD is characterized by the presence of choroidal neovascularization (CNV), pathologic new vessels from the choroid that grow into the avascular outer retina through breaks in Bruch's membrane (BM). CNV can lead to subretinal hemorrhage, fluid exudation, lipid deposition, detachment of the retinal pigment epithelium from the choroid, fibrotic scars, or a combination of these (Jaeger R et al, 2008 supra; De Jong P, *N Engl J Med* 355, 1474-1485 (2006); Donoso L et al, *Surv Ophthalmol* 51, 137-152 (2006); Stanga P et al, *Ophthalmol* 110, 15-21 (2003); incorporated by reference herein). Fluorescein (FA) and/or indocyanine green angiography (ICGA) have traditionally been used to detect and assess CNV in the clinic. However, these techniques are two-dimensional (2D) and involve intravenous dye injections, which can lead to nausea and anaphylaxis (Lopez-Saez M et al, *Ann Allergy Asthma Immunol* 81, 428-430 (1998); incorporated by reference herein).

Optical coherence tomography (OCT) is a noninvasive, depth resolved, volumetric imaging technique that is commonly used to visualize retinal morphology (Huang D et al, *Science* 254, 1178-1181 (1991); incorporated by reference herein). A limitation of conventional structural OCT is that it cannot be used to detect blood flow or discriminate vascular tissue from surroundings. To address this limitation, several OCT angiography methods have been proposed to identify blood flow at the microcirculation level (An L et al, *Opt Express* 16, 11438-11452 (2008); Yasuno Y et al, "*Opt Express* 15, 6121-6139 (2007); Grulkowsk I et al, *Opt Express* 17, 23736-23754 (2009); Fingler J et al, *Opt Express* 17, 22190-22200 (2009); Liu G et al, *Opt Express* 19, 3657-3666 (2011); incorporated by reference herein). Among these OCT angiography methods, the split-spectrum amplitude-decorrelation angiography (SSADA) algorithm is able to distinguish blood flow from static tissues based on detecting the reflectance amplitude decorrelation over consecutive cross-sectional B-scans at the same location (Jia Y et al, *Opt Express* 20, 4710-4725 (2012); Gao S et al, *Opt Lett* 40, 2305-2308 (2015); incorporated by reference herein). Moreover, segmentation of SSADA-based OCT angiograms can identify CNV as blood flow in the outer retina, a region devoid of blood flow in healthy eyes (Jia Y et al, *Ophthalmology* 121, 1435-1444 (2014); Jia Y et al *Proc Natl Acad Sci USA* 112, E2395-2402 (2015); de Carlo T et al, *Ophthalmology* 122, 1228-1238 (2015); Spaide R, *Am J Ophthalmol* 160, 6-16 (2015); Kuehlewein L et al, *Eye (Lond)* 29, 932-935 (2015); incorporated by reference herein). Despite these advances in OCT angiography delineation of CNV lesions from such datasets remains a challenge. The simplest method involves manual delineation by an experienced expert, but this approach is subjective, operator intensive, and time-consuming. Thus, a reliable and robust automatic detection method for quantifying the CNV lesion is needed in order to maximize the clinical utility of OCT angiography in the diagnosis of CNV and evaluation of the therapeutic effect of different treatments.

SUMMARY

Disclosed herein is an image processing method for use in OCT angiography that detects and quantifies CNV in the outer retina of the eye. The method involves receiving a set of cross sectional angiograms, separating that set of angiograms into two distinct subsets representing the inner retina and outer retina, and then projecting the maximum flow values in each subset to produce a pair of 2D en face angiograms, referred to hereafter as the inner retina angiogram and the outer retina angiogram. The inner retina angiogram is filtered to remove noise and then subtracted from the outer retina angiogram to reduce projection artifacts from the deeper outer retina angiogram. The resultant outer retina angiogram image is submitted to a pattern recognition analysis wherein a multiscale saliency map is generated. This saliency map is processed using a nonlinear filtering approach to smooth within the target region while enhancing edges within the saliency map. Finally a binary vascular mask is generated from the edge-enhanced saliency map using thresholding and morphological operations. This binary vascular mask is applied to the original 2D en face outer retina angiogram to extract the CNV area contained therein.

Also disclosed herein are tests of the algorithm performance in terms of repeatability and in comparison of automated versus manual delineation. Further, using the manual delineations as the standard, false positive error and false negative error rates are calculated for the disclosed algorithm.

It is an object of the invention to overcome problems with projection artifacts that cast shadows from the more superficial inner retina onto the deeper outer retina where CNVs may manifest.

It is an object of the invention to overcome problems with distinguishing the boundary between CNV and non-CNV background by incorporating a multiscale saliency model to enhance contrast.

It is an object of the invention to output a visualization and a quantification of CNV area that a clinician could use for disease assessment and monitoring.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

BRIEF DESCRIPTION OF THE SEVERAL VIEWS OF THE DRAWINGS

FIG. 2 is a pictorial flowchart depicting the segmentation algorithm described in (Jia Y et al, 2014 supra) and the disclosed method for automated saliency-based segmentation of choroidal neovascularization (CNV). A) Original outer retina angiogram of a patient with neovascular age-related macular degeneration (AMD) showing artifacts and CNV. (B1) Inner retinal large vessel mask used to subtract large vessel projections from the outer retina. (B2) Filtered inner retina used to subtract artifacts from the outer retina. (C1) Outer retina with large vessel projections removed. (C2) Outer retina with artifacts removed. (D1) Gaussian filtering to reduce the remaining artifacts. (D2) Saliency map showing the CNV region. (E1) CNV area obtained by a threshold operator. (E2) CNV area obtained by multiplying the CNV membrane mask and original en face outer retinal angiogram and using a threshold operator. (F1) Multi-scale saliency results showing intermediate results of calculating the saliency map. (F2) Post-processing procedure including nonlinear filtering to enhance the boundaries and smooth the saliency map, Otsu's method for determining the threshold, and morphological operations for obtaining the CNV membrane mask. (A, B2, C1, C2, D1) The display scale of decorrelation values ranges from 0.025 to 0.25.

DETAILED DESCRIPTION

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth.

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a one-to-one correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a projection of the three dimensional dataset onto a single planar image called an en face angiogram (Wallis J et al, *Med Imaging IEEE Trans* 8, 297-230 (1989); Wang R K et al, 2007 supra; Jia Y et al, 2012 supra); incorporated by reference herein). Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer can be used to generate a 2D en face angiogram of the inner retina). Once generated, the en face angiogram image may be used to quantify various features of the retinal vasculature as described herein. This quantification typically involves the setting of a threshold value to differentiate, for example, the pixels that represent active vasculature from static tissue within the angiogram. These 2D en face angiograms can be interpreted in a manner similar to traditional angiography techniques such as fluorescein angiography (FA) or indocyanine green (ICG) angiography, and are thus well-suited for clinical use.

Optical coherence tomography angiography has recently been used to visualize choroidal neovascularization (CNV) in patients with age-related macular degeneration. Identification and quantification of CNV area is important clinically for disease assessment. An automatic algorithm for CNV area detection is presented herein. It relies on denoising and a saliency detection model to overcome issues such as projection artifacts and the heterogeneity of CNV. Qualitative and quantitative evaluation was performed on scans of 5 patients. The automated algorithm agrees well with manual delineation of CNV area.

Identification and quantification of CNV from OCT angiography datasets poses a number technical challenges. First, OCT angiography is susceptible to shadowgraphic flow projection artifacts. Due to strong light absorption of blood cells, blood vessels cast shadows in depth on structural OCT. Reflectance amplitude decorrelation in the blood vessel due to flow is carried in the shadow. As a result the vascular pattern from the superficial inner retina is replicated on the deeper outer retina, compromising the clarity of the more deeply imaged structures. Second, while the effect of eye motion during the scan can be minimized by subtracting bulk motion noise (Jia Y et al, 2012 supra; Jia Y et al, *Ophthalmol* 121, 1322-1332 (2014); incorporated herein by reference) and using orthogonal registration (Kraus M et al, *Biomed Opt Express* 5, 2591-2613 (2014); incorporated by reference herein), motion artifacts in the form of horizontal or vertical lines may remain. Finally, the intrinsic complexity of CNV also makes automated detection difficult. The shape, size, location, and velocity of flow of the CNV can vary between patients, and the boundary between CNV and what is not CNV, the background, can be hard to distinguish with conventional automated detection techniques. Thus, accounting for artifacts and for the complexity of the CNV lesion are key problems which need to be solved.

Methods to segment and analyze vascular structures from fundus or FA images have been based on structure enhancement filters (Frangi A et al, *MICCAI'98*, 130-137 (1998); Law M et al, *ECCV*, 368-382 (2008); incorporated by reference herein) and/or geodesic methods Chen D et al, in *Scale Space and Variational Methods in Computer Vision*, 270-281 (2015); incorporated by reference herein). However, few works have been published about segmentation of CNV from OCT angiography images (Jia Y et al, 2014 supra). Because the CNV lesion is dissimilar from projection and motion artifacts, saliency based detection methods were employed herein (Borji A et al, *IEEE Trans Pattern Anal Mach Intell* 35, 185-207 (2013); incorporated by reference herein). Briefly, saliency describes an abstraction of how the human visual system characterizes regions or objects which stand out from their surrounding parts. Saliency based methods attempt to replicate this process for the detection of dominant objects in a scene based on various image features. In this disclosure, an automatic segmentation algorithm, termed "saliency algorithm", that is dedicated to CNV recognition in outer retina en face angiograms from OCT angiography is described.

Algorithm Overview

Figure 1:
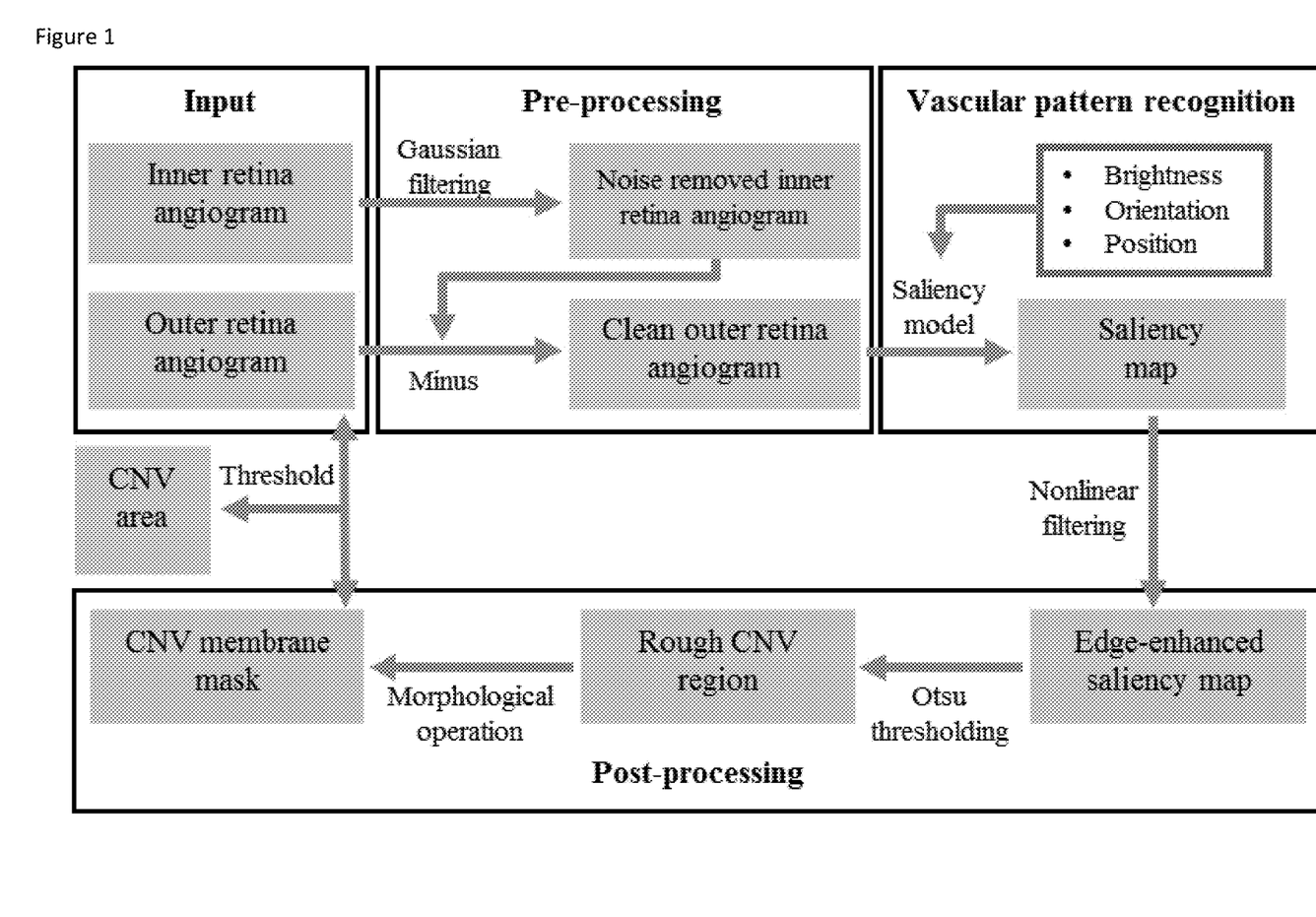
FIG. 1 is a flowchart of a method of detecting choroidal neovascularization (CNV).

An overview of the disclosed algorithm is shown in FIG. 1. A pre-processing step was first performed to reduce projection artifacts from the outer retina. After denoising, the CNV region was more distinctive. Vascular pattern recognition through a saliency model followed. Finally, post-processing steps based on nonlinear filtering, thresholding, and morphological operations were applied to generate a CNV membrane mask. The following three sections will describe the process in detail. The algorithm was implemented with custom software written in Matlab 2011a (Mathworks, Natick, Mass.).

Pre-Processing

Retinal circulations are primarily transverse to the OCT light beam and are best visualized by projecting the volumetric data set as 2D en face images. Anatomical landmarks from structural OCT reflectance images were used to guide semi-automated segmentation to separate circulations based on depth (Tan O et al, *Ophthalmol* 115, 949-956 (2008); incorporated herein by reference). Maximum flow projection between the internal limiting membrane (ILM) and outer plexiform layer (OPL) generated the en face inner retina angiogram, representing retinal circulation. Maximum flow projection between the outer boundary of OPL to BM generated the en face outer retina angiogram, normally an avascular region. CNV grows from the choroid through BM and often is directly adjacent to the retinal pigment epithelium (RPE). Inner retinal vessels project artifact onto the RPE, due to its high reflectance on structural OCT. This projection artifact in the outer retina angiogram interferes with CNV detection.

Angiographic projection and motion artifact ideally need to be minimized prior to application of the saliency method. In previous work (Jia Y et al, 2014 supra), a binary large inner retinal vessel map was used to mask vessel projections on the outer retinal angiogram. However, it can be difficult to determine the appropriate threshold for obtaining such a vessel mask. If the threshold value is too low, the mask can contain smaller inner retinal vessels which can remove some useful information in the CNV region. Alternatively, masking only large vessels may leave small inner retina vessel projections that are difficult to differentiate as projection artifact versus CNV. In the algorithm disclosed herein the inner retina angiogram is filtered by a 20×20 pixel Gaussian filter with a sigma value of 0.1. The filtered inner retina angiogram is then subtracted from the outer retina angiogram. The resulting image better highlighted the CNV region, but still contained small, bright discrete noise areas.

Vascular Pattern Recognition

Because the CNV becomes more distinct in the outer retina angiogram after artifact removal, saliency based detection is an effective and robust method to delineate its structure. Detection accuracy depends on both the distinctiveness of the target object and the homogeneity and/or blurred degree of the background. As a result of projection removal, some parts of the CNV region became discontinuous and fuzzy. Therefore, the saliency model should detect not only the salient region and but also neighboring regions. A context-aware saliency detection method was employed to account for the above issues. This method combines context-awareness and saliency detection with the aim of detecting the prominent objects and the parts of the background that contain similar contextual information (Goferman S et al, *IEEE Trans Pattern Anal Mach Intell* 34, 1915-1926 (2012); incorporated herein by reference).

Context-aware saliency detection borrows from some basic principles associated with human visual attention: local low-level considerations such as brightness and contrast, global considerations to ignore reoccurring features, and visual organization rules regarding object center(s) of gravity. For many image processing applications, local and global considerations incorporate color information, but OCT angiography is simplified in the sense that it produces what can be considered grayscale en face images. In the present disclosure, brightness, orientation contrast, and positional distance were used together to define a measure of distinctiveness. In the en face outer retinal angiogram, each pixel i was assessed. The local context of pixel i was given by considering its surrounding pixels in a 7×7 pixel patch centered on the pixel. The saliency of each pixel i depends on the distinctiveness of its patch. The quantity $d_{bright}(p_i,p_j)$ was defined as the Euclidean distance between the summed intensities of patches $p_i$ and $p_j$ in the grayscale image, normalized to the range [0,1].

However, because there were still some small, bright non-CNV areas in the projection-removed angiogram, brightness information alone was not sufficient to delineate CNV. Therefore, the local orientation information (Itti L et al, *IEEE Trans Patt Anal Mach Intell* 20, 1254-1259 (1998); incorporated herein by reference) was incorporated to aid in the determination of what is of interest. The local orientation information was obtained utilizing Gabor filters, which are a product of a cosine grating and 2D Gaussian envelope, at four preferred orientations $\theta \in \{0°, 45°, 90°, 135°\}$. The size of the Gabor kernel was 31×31 pixels. The Euclidean distance $d_{orientation}(p_i,p_j)|_\theta$ between patches $p_i$ and $p_j$ was calculated as the orientation contrast at the corresponding orientation $\theta$:

$$d_{orientation}(p_i, p_j) = \frac{1}{N} \sum d_{orientation}(p_i, p_j)\Big|_\theta \quad (1)$$

where $\theta=0°$, $45°$, $90°$, $135°$ and N=4. This was also normalized to the range [0,1]. In the projection-removed outer retina angiogram, CNV regions were grouped together. Thus, a metric $d_{position}(p_i,p_j)$ was defined as the positional distance between patches $p_i$ and $p_j$. The distinctiveness between two patches was then defined as $$d(p_i, p_j) = \frac{d_{bright}(p_i, p_j) + d_{orientation}(p_i, p_j)}{2(1 + c \cdot d_{position}(p_i, p_j))} \quad (2)$$

where c=3. The distinctiveness measure considers the local and global information simultaneously. It is proportional to the difference in appearance represented by brightness and orientation contrast and inversely proportional to the positional distance. Pixel i is considered salient when $d(p_i,p_j)$ is high for all j.

Multi-scale saliency detection was further incorporated to decrease the saliency of background and enhance the contrast between salient and non-salient areas. Typically background patches are more likely to be similar at multiple scales, while the dominant object is salient and could have similar patches at a few scales but not at all of them. Because using multiple scales increases computation time, a simplified approach using only comparisons to only the K most similar patches was adopted. The saliency value of pixel i at a single-scale r was then defined as $$S_i^r = 1 - \exp\left\{-\frac{1}{K} \sum_{k=1}^{K} d(p_i^r, q_k^r)\right\} \quad (3)$$

where $q_K$ belongs to the identified K most similar patches and K=65. When searching for the K most similar patches, patches of 7×7 with 50 percent overlap were considered.

The saliency of pixel i at scale r was determined from the K most similar patches at multiple scales $R_q=\{r,(½)r,(¼)r\}$.

At each scale r, the saliency map was normalized to the range [0,1] and interpolated back to original image size of 304×304 pixels. Equation 3 was refined as $$S_i^r = 1 - \exp\left\{-\frac{1}{K}\sum_{k=1}^{K} d(p_i^r, q_k^{r_k})\right\} \quad (4)$$

where $r_k \in R_q$. The final saliency value for pixel i was the mean of all patches $p_i$ at different scale r.

$$\overline{S}_i = \frac{1}{M}\sum_{r \in R} S_i^r \quad (5)$$

Four scales were used, R={100%, 80%, 50%, 30%}.

A final consideration was that areas close to the attention foci are supposed to be more distinctive than those regions far away. The visual contextual effect was simulated. A threshold operation was applied to extract the most attended localized areas from the saliency map, which contained all the pixels with their saliency value greater than a threshold of 0.8. The saliency value of pixels outside the most attended localized areas was redefined according to its Euclidean distance $d_{foci}^r(i)$ of position to the closest attended pixel at scale r, normalized to range [0,1]. The saliency of each pixel was modified as $$\hat{S}_i = \frac{1}{M}\sum_{r \in R} S_i^r (1 - d_{foci}^r(i)) \quad (6)$$

After this step, the saliency value of the interesting background in the neighborhood of the salient objects will be increased. This allowed for the inclusion of the neighboring regions to ensure all the CNV was detected.

Generation of the Vascular Mask

The integration of multi-scale enhancement and context-awareness led to a saliency map that approximated the CNV region. However, it was difficult to determine the threshold to extract the CNV region from the saliency map as the map was usually blurred at boundaries. To address the issue of blurred boundaries, a Laplacian edge detection filter was first used on the saliency map. In parallel, the bilateral filter proposed by (Tomasi C et al, *IEEE Sixth Int Conf Comp Vis* Bombay (1998), 839-846; incorporated herein by reference) was used to smooth within the target region and preserve the boundary. This bilateral filter was a weighted average operation process. Unlike the traditional Gaussian filter which utilizes only position information as the weight, the weight of the shift-invariant Gaussian filter belonging to the bilateral filter contains both position distance and intensity information. After bilateral filtering, the boundary information detected by the Laplacian edge detection operator was used to enhance the boundaries. Otsu's threshold method was used to extract the rough CNV region, after which some small, discrete regions still remained. Morphological operations were then used to remove small areas (<80 pixels) and fill holes. Finally, the CNV membrane mask was obtained. It was a binary image by which the original en face outer retina angiogram was multiplied to extract the CNV. A threshold operator was used to calculate the CNV area.

EXAMPLES

Example 1—Methods

Data Collection

Patients were selected from those diagnosed with neovascular AMD at the Casey Eye Institute Retina Service based on clinical presentation, examination, and fluorescein angiography. Patients were enrolled after informed consent in accordance with an Institutional Review Board/Ethics Committee-approved protocol at Oregon Health & Science University and in compliance with the Declaration of Helsinki.

Two volumetric datasets were collected from single eyes of 5 patients with neovascular AMD. All of the data was collected using a commercial 70 kHz spectral domain OCT system with a center wavelength of 840 nm (RTVue-XR, Optovue, Calif.). The macular angiography scan protocol for a single volumetric dataset contained 2 scans covering a 3×3 mm area. Each scan comprised of 304×304×2 A-scans acquired in less than 3 seconds. The fast scanning direction was in the horizontal direction for the first scan and in the vertical direction for the second. The SSADA algorithm was applied to detect flow between the 2 consecutive B-scans at the same location (Jia Y et al, *Opt Express* 20, 4710-4725 (2012); Gao S et al, *Opt Letters* 40, 2305-2308 (2015); incorporated herein by reference). The two scans were then registered and merged through an orthogonal registration algorithm (Kraus M et al, 2014, supra; incorporated by reference herein).

Sixteen participants were recruited. Data from 6 participants were excluded due to low image quality (structural OCT signal strength index <50), severe motion artifacts, and/or shadowing due to pigment epithelial detachment. Data from 3 other participants were excluded because an experienced grader could not identify the presence of CNV on OCT angiography. Data from the remaining 7 participants were used in this study.

Verification of Results

The algorithm results were compared to output from the algorithm used in a previous study, termed the "previous algorithm" (Jia Y et al, 2014 supra), and results from manual delineation of the CNV. The within-visit repeatability was assessed for the automated previous algorithm described, the disclosed automated saliency algorithm, and manual delineation using coefficient of variation (CV) and intraclass correlation (ICC). For manual delineation, the CNV was contoured by an experienced grader, and a threshold operator was used to calculate the CNV area.

To compare the results from the two automated algorithms to that from manual delineation, the Jaccard similarity metric was used, which is defined as $$J(I_s, I_m) = |I_s \cap I_m|/|I_s \cup I_m| \quad (7)$$

where $I_s$ is the segmentation result from one of the automated pipelines and $I_m$ is the result from manual delineation. The Jaccard coefficient ranges from 0 to 1, where 1 denotes that the two were identical and 0 if they were completely dissimilar. Using the manual delineation results as the standard, errors rates were also computed. False positive error was the ratio of the total number of automatically segmented pixels that were not included in the manual segmentation result to the total number of manually segmented pixels. False negative error was the ratio of the total number of manually segmented pixels that were not included in the automatic segmentation result to the total number of manually segmented pixels (Lee J et al, Comp Methods Programs Biomed 88, 26-38 (2007); incorporated herein by reference).

Results for a Single Patient

Figure 2:
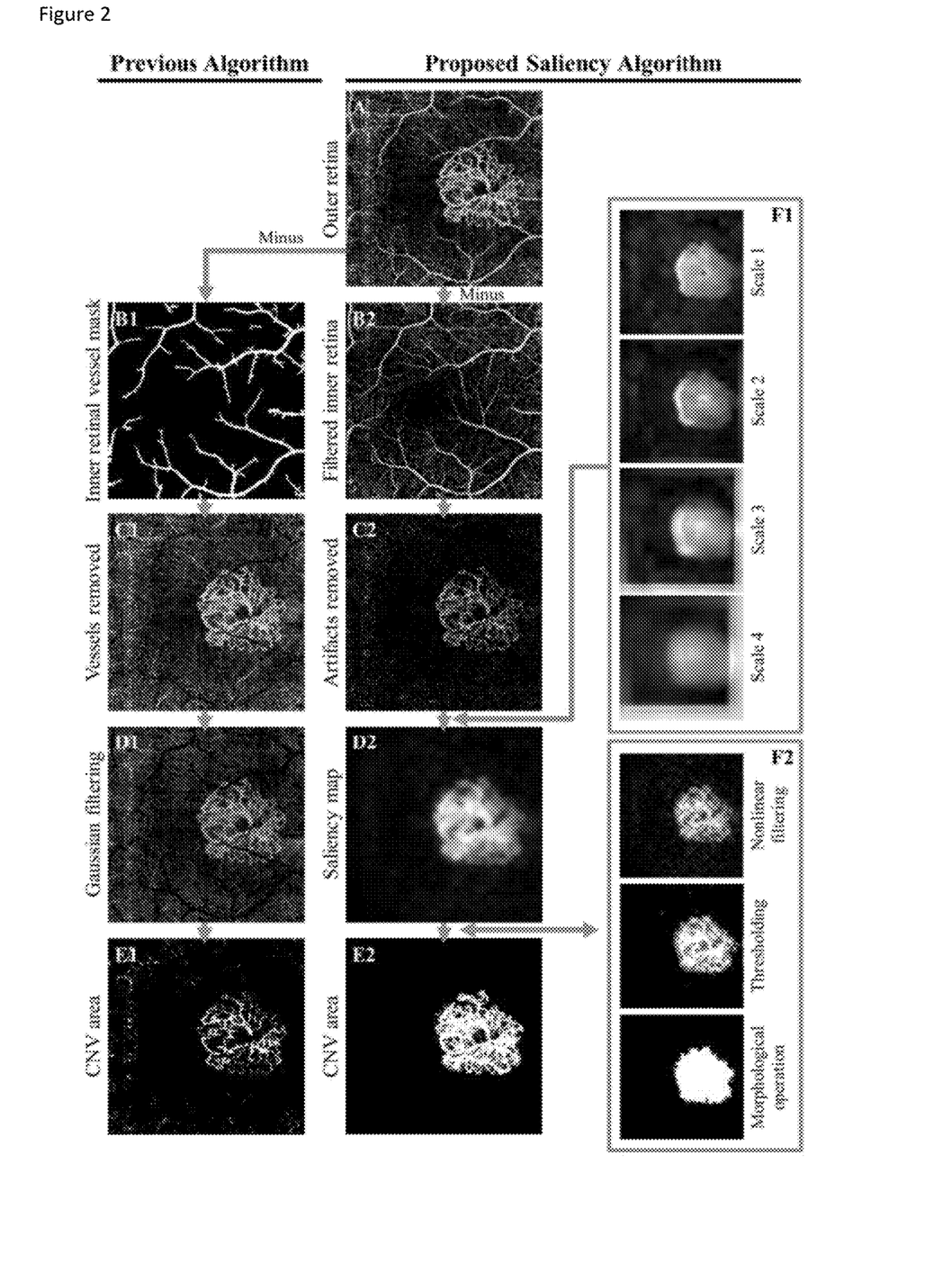

The en face outer retinal angiogram from a participant with neovascular AMD was used to show the workflow of the previous algorithm and the saliency algorithm. FIG. 2A shows the original outer retina angiogram with CNV and artifacts. The left column illustrates the process using the previous algorithm. The mask of inner retina vessels shown in FIG. 2B1 was used to remove the large vessels projections from the outer retina. The result shown in FIG. 2C1 still has some small vessel projections and motion artifacts. The previous algorithm then applies a Gaussian filter to reduce the remaining artifacts (FIG. 2D1). For the final step, a threshold operator was used to extract the CNV area (FIG. 2E1). However, artifacts still remained after the mask subtraction and Gaussian filtering, leading some artifacts to be misclassified as CNV.

In the disclosed saliency algorithm, the inner retina angiogram was first smoothed by a 20×20 pixel Gaussian filter to produce the filtered inner retina shown in FIG. 2B2. By subtracting the filtered inner retina from the outer retina most of the projection artifacts were removed (FIG. 2C2) and some CNV signal was also reduced. However, the CNV area became more distinctive in the outer retina. Then, a context-aware saliency model based on brightness, orientation, and position information was used to detect the CNV region (FIG. 2C2). The saliency calculation was done at multiple scales (FIG. 2F1) and combined into a single saliency map (FIG. 2D2). To aid in the segmentation of the CNV, an edge-enhanced nonlinear filter was used to smooth the CNV region and enhance the boundary. Next, Otsu's method was used to determine the threshold. Finally, morphological operations were used to remove small isolated regions and fill holes to obtain the CNV membrane mask. These post-processing steps are shown in FIG. 2F2. The en face outer retinal angiogram was multiplied by the CNV membrane mask, and a threshold operator was used to determine the CNV area (FIG. 2E2).

Results from Seven Patients

Figure 3:
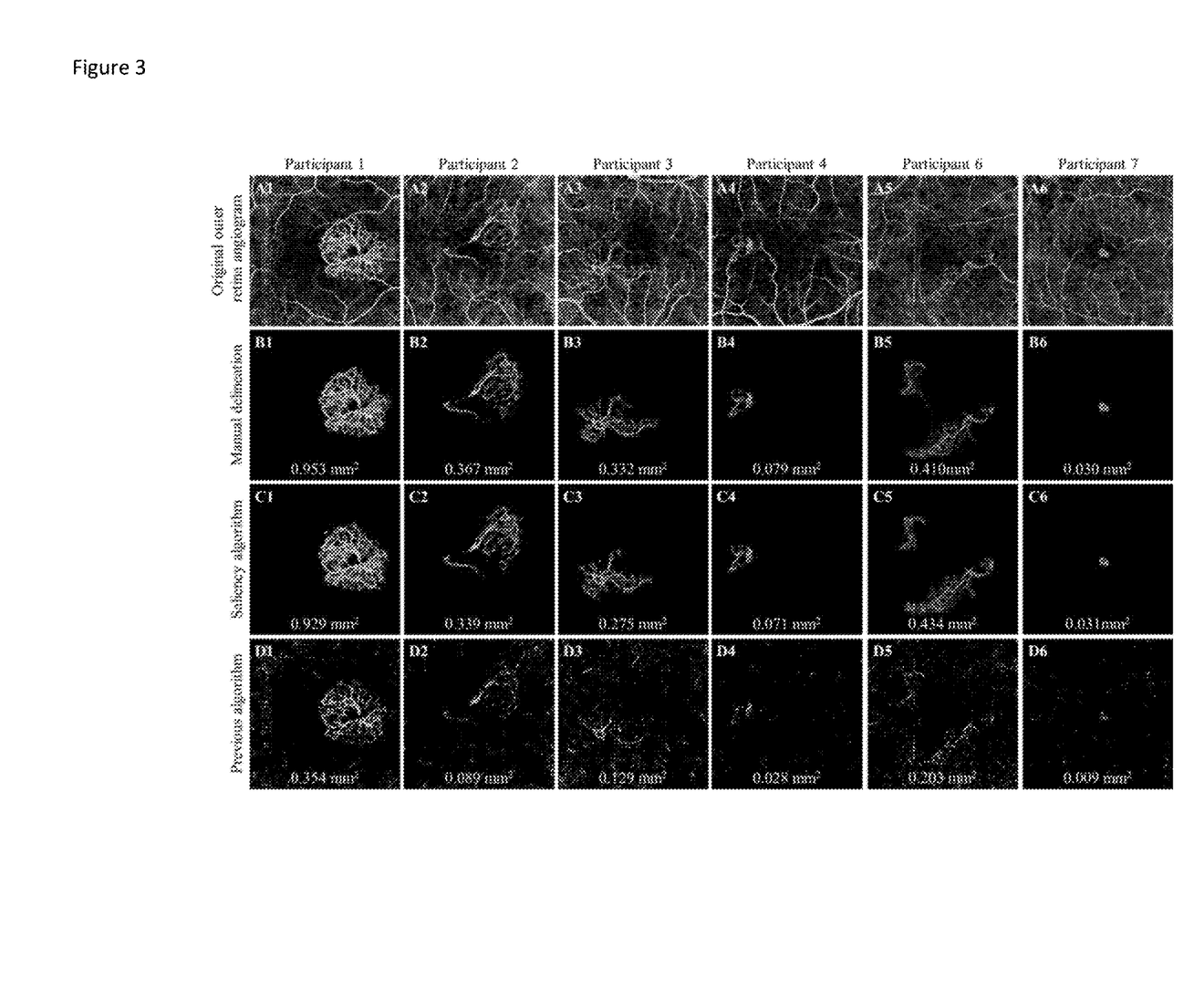
FIG. 3 is a grid of images depicting en face OCT angiograms retinal angiograms from all participants except for participant #5 which is shown in FIG. 4. The top row (A1-6) shows the en face maximum flow projection angiogram from the outer retinal slab without any additional processing. The second row (B1-6) shows the results of manual delineation of CNV by an expert human. The third row (C1-6) shows the results from the automated saliency algorithm. The bottom row (D1-6) shows the results from the previous automated algorithm. CNV areas, as delineated by a grader or algorithm, are shown below each processed image. The display scale of decorrelation values ranges from 0.025 to 0.25 for all images.
Figure 4:
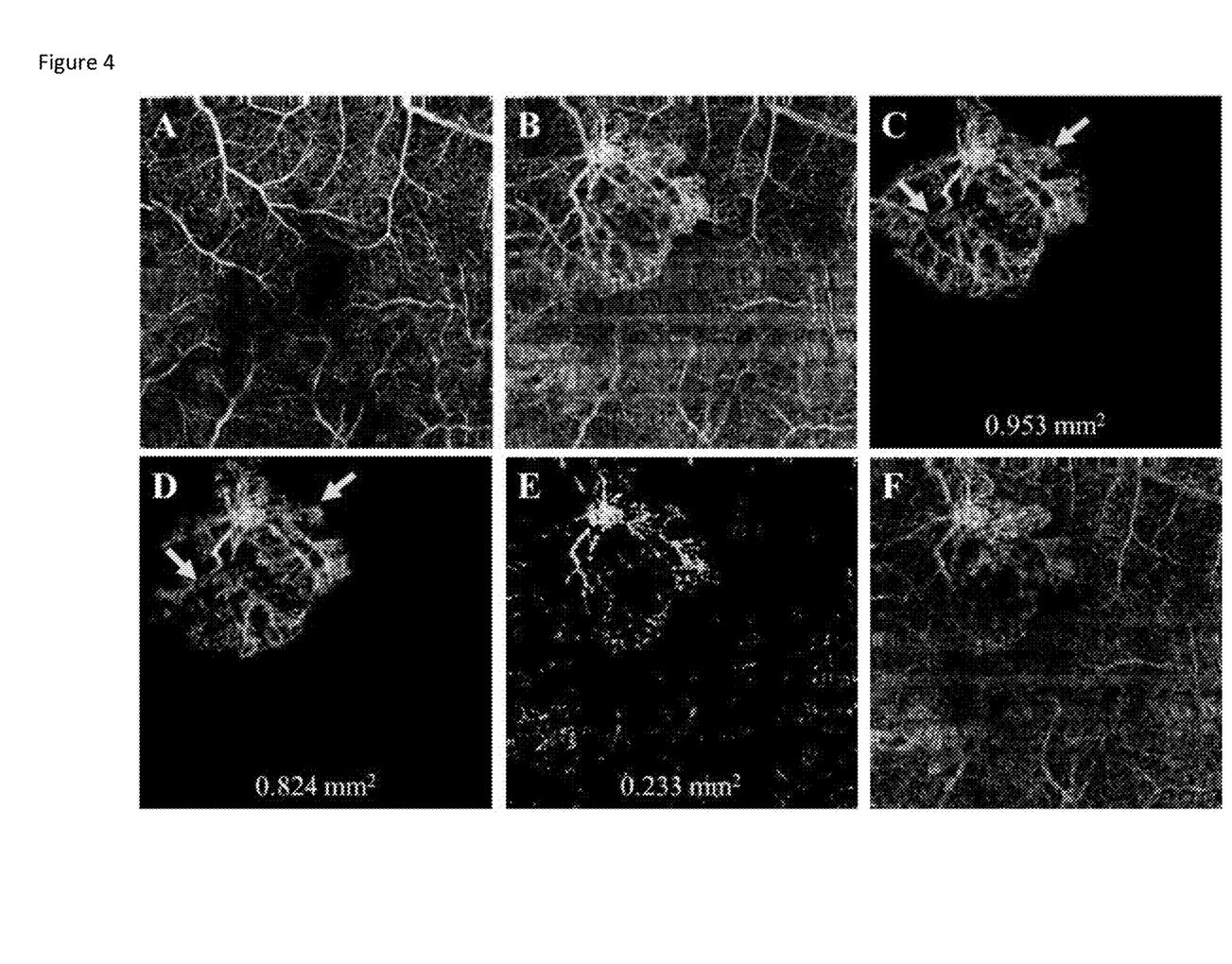
FIG. 4 is a grid of images depicting en face OCT angiograms from the case (participant #5) where there was the greatest difference in CNV area between the saliency algorithm and expert manual grading. (A) Inner retinal angiogram. (B) Outer retinal angiogram without any additional processing. (C) Manual delineation of CNV by an expert human. (D) Automated saliency algorithm. Yellow arrows highlight points of interest for comparison between C and D. (E) Previous automated algorithm. CNV areas, as delineated by a grader or algorithms, are shown below each processed image. (F) Choriocapillaris angiogram without any additional processing. The display scale of decorrelation values ranges from 0.025 to 0.25 for all images.

The results from the disclosed saliency algorithm were compared with results from the previous automated algorithm and with results obtained by manual delineation of the CNV. Scans of a single eye of seven (7) patients with AMD were analyzed. Two volumetric datasets from each eye were evaluated to assess within-visit repeatability. The results from one dataset of each subject are shown in FIG. 3 and FIG. 4. The cases included both type I and type II (participants #1, 5) CNV membranes with a wide range of sizes. An expert human grader delineated the boundary of the CNV membrane on the en face maximum flow projection angiogram of the outer retinal slab, while also viewing the inner retinal angiogram. The saliency algorithm automatically outlined the CNV boundary and calculated CNV area. The algorithm required 17.5 seconds to execute on an Intel Xeon CPU (E3-1226, 3.3 Ghz), of which 94% of the time was spent on generating the saliency map. FIGS. 3B1 to 3B6 show the manual delineation results whereby a grader contoured the CNV. Because no vessel projection removal was utilized in this method, the manual delineation results are potentially overestimates. FIGS. 3C1 to 3C6 show the results of the disclosed saliency algorithm. FIGS. 3D1 to 3D6 are the segmented results produced by the previous algorithm.

Qualitatively, the results from the disclosed saliency algorithm were closely matched to those from manual delineation. However, the saliency algorithm tended to include less area from the CNV due to the projection artifact removal step. This is highlighted in the results from participant #5 in FIG. 4 (compare the respective regions as indicated by yellow arrows in FIGS. 4(C) and 4(D)). The previous algorithm also identified similar shapes for the CNV membranes, but did not cleanly remove scattered background noise due to projection and motion artifacts. The continuity of the CNV network was also often broken up by the higher decorrelation threshold used. It was clear that the previous algorithm differed more from manual CNV grading, and this poor agreement was reflected in the Jaccard similarity metric, false negative, and false positive CNV pixel identification rates (Table 1). In contrast, the saliency algorithm agreed well with manual grading. The saliency algorithm was significantly better than the previous algorithm in all

TABLE 1

Agreement Between Automated Algorithms and Manual Grading of Choroidal Neovascularization

|  | Previous Algorithm | Disclosed Saliency Algorithm | P-value |
| --- | --- | --- | --- |
| Jaccard similarity metric | 0.157 ± 0.059 | 0.834 ± 0.125 | <0.001 |
| False positive error | 0.120 ± 0.066 | 0.043 ± 0.046 | 0.001 |
| False negative error | 0.826 ± 0.059 | 0.134 ± 0.109 | <0.001 |

Measures of agreement were computed on a pixel-by-pixel basis from graded en face angiograms of choroidal neovascularization. Mean ± standard deviation of the Jaccard similarity metric and error rates were computed from 7 participants. P-values were based on the paired Wilcoxon rank-sum test.

Repeatability of CNV area measurement was calculated from the 2 sets of OCT angiography scans obtained from each participant. All methods had relatively good repeatability as measured by CV and ICC (Table 2).

TABLE 2

Repeatability of Choroidal Neovascularization Quantification

|  | Manual | Proposed Saliency Algorithm | Previous Algorithm |
| --- | --- | --- | --- |
| CV | 3.90% | 6.70% | 7.15% |
| ICC | 0.998 | 0.992 | 0.993 |

Abbreviations: coefficient of variation (CV); intraclass correlation (ICC), Data was from 7 participants.

Superior Performance of Saliency-Based Model in 840 nm OCT System

Figure 5:
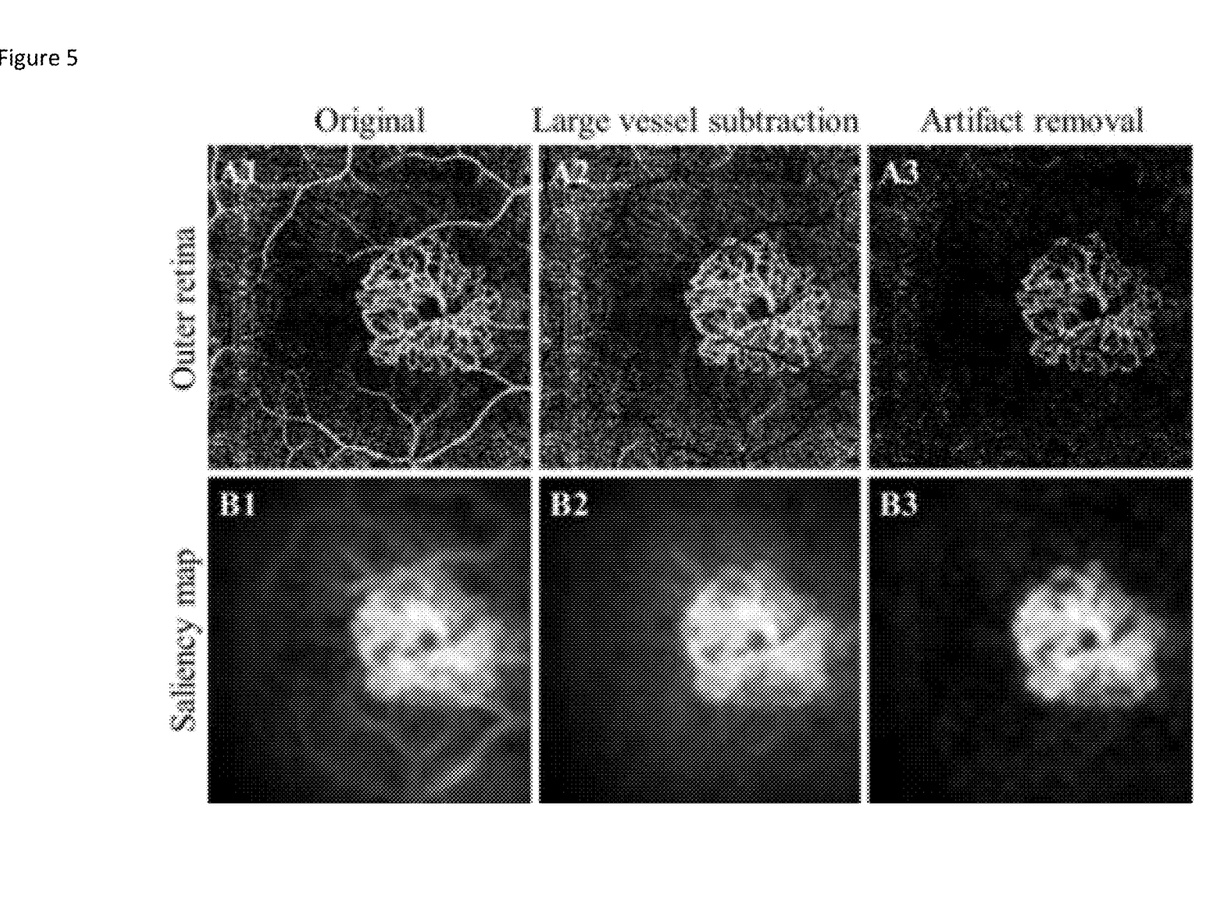
FIG. 5 is a set of images depicting the results of image processing operations used to delineate CNV in OCT volumetric images. (A1) Original outer retina angiogram. (A2) Outer retina angiogram with inner retinal large vessel subtracted leaving motion artifacts and small vessel projections. (A3) Outer retina angiogram with both large and small retinal vessels subtracted. (B1) Saliency map computed from A1 shows the CNV outline but is contaminated with large retinal vessel pattern. (B2) Saliency map computed from A2 shows CNV outline but is cluttered with a background haze. (B3) Saliency map computed from A3 shows a clean CNV pattern. (A1 to A3) The display scale of decorrelation values ranges from 0.025 to 0.25.

The previous algorithm had worked well using OCT angiography obtained using a 1050 nm swept-source OCT system. The projection artifact from the inner retinal vessel onto the outer retina was much sparser at that longer wavelength and consisted of mainly a large vessel pattern; therefore the CNV pattern was not as severely disrupted by the projection artifact. However, in the 840 nm spectral domain OCT system employed in the examples described herein, the shadow cast by the inner retinal vessels was much stronger due to the shorter wavelength used by the device. Therefore the projection artifact included not only larger retinal vessels but also fine capillary patterns. The removal of this much denser projection artifact disrupted the CNV pattern much more severely. Therefore the saliency map was needed to restore the CNV outline. The Gaussian filter and thresholding employed by the previous algorithm were not adequate to the task. FIG. 5 illustrates the problem with dense inner retinal projection. Both the subtraction of all projection artifacts and the saliency map steps were necessary to obtain a clean outline of the CNV.

Summary of Example 1

OCT angiography is a new imaging approach to visualizing CNV. The disclosed algorithm for CNV area quantification involves 4 main steps: (1) minimize projection artifacts in the outer retina angiogram by subtracting the inner retinal vessel pattern; (2) identify the CNV area by a context-aware saliency model based on brightness, orientation, and position information to identify CNV; (3) enhance the saliency map by nonlinear filtering, and (4) calculate CNV area from flow pixels within the CNV boundary. It was shown that the disclosed algorithm could detect and quantify the CNV in neovascular AMD cases with a variety of CNV patterns. The saliency algorithm agreed with expert human grading much better than the previous algorithm. The previous algorithm had a notably high false negative rate of 0.826 (Table 1) because the steps of subtracting large inner retinal vessel projection and thresholding also removed flow signal in the CNV. Identification of the CNV through the saliency map helped to restore the outline of the CNV after removal of projection artifact.

Example 2—Optical Coherence Tomography Angiography Image Processing System

Figure 6:
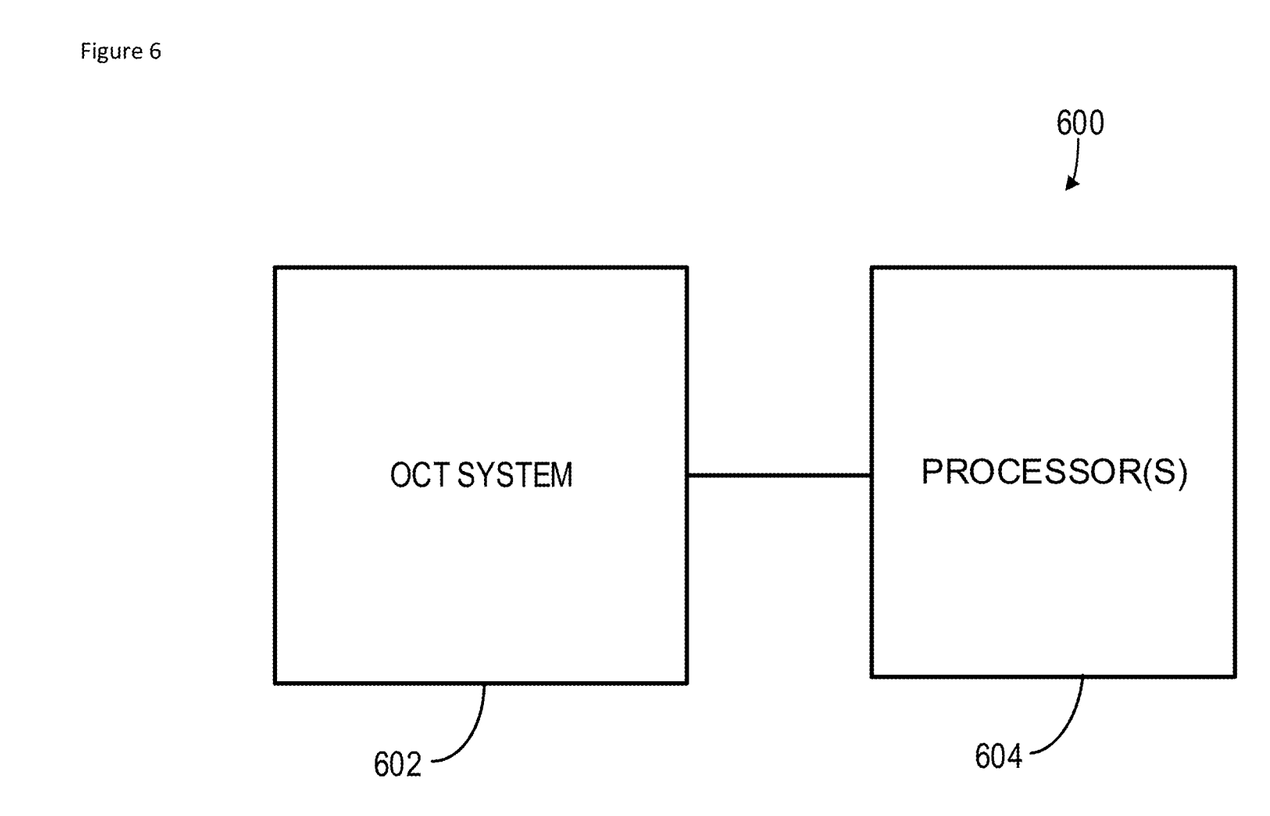
FIG. 6 is a schematic of a system for processing OCT angiography data in accordance with the disclosure.

FIG. 6 schematically shows an example system 600 for OCT image processing in accordance with various embodiments. System 600 comprises an OCT system 602 configured to acquire an OCT image comprising OCT interferograms and one or more processors or computing systems 604 that are configured to implement the various processing routines described herein. OCT system 600 can comprise an OCT system suitable for OCT angiography applications, e.g., a swept source OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the method depicted in FIGS. 1-6 described above, can be implemented as a computer application, computer service, computer API, computer library, and/or other computer program product.

Figure 7:
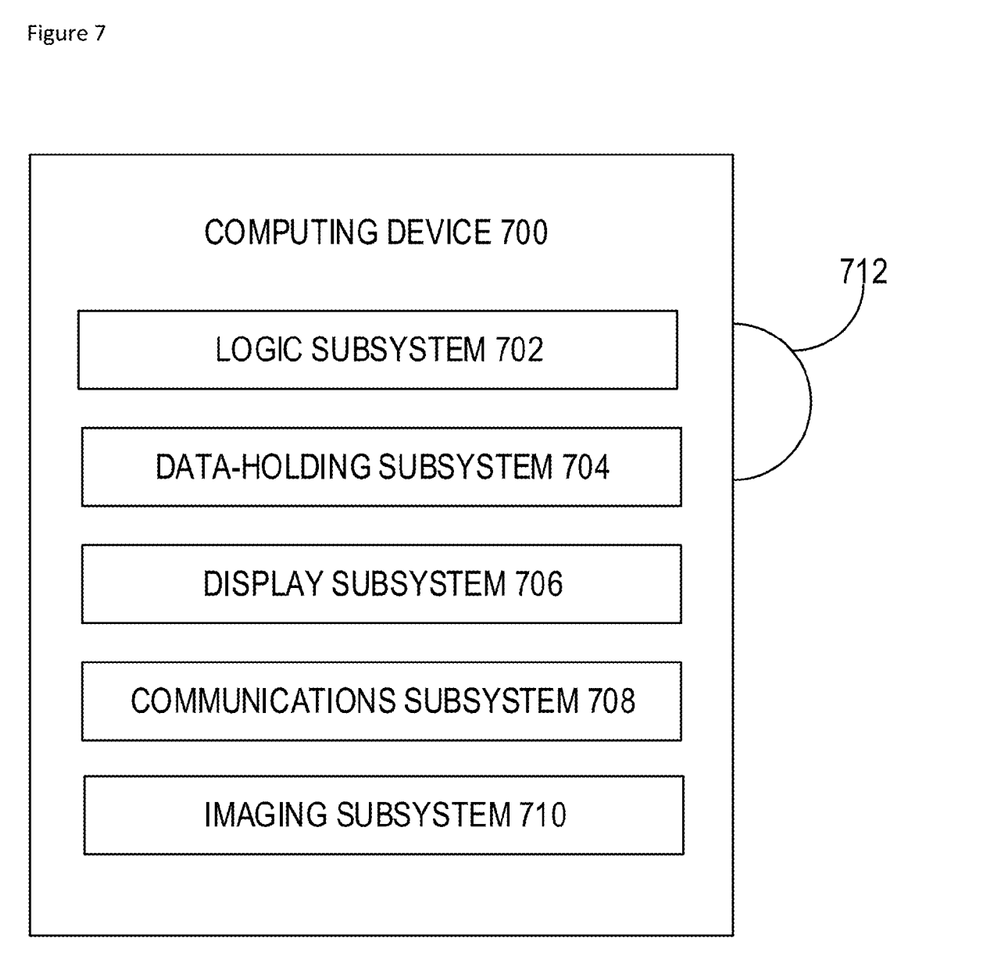
FIG. 7 is an example of a computing system in accordance with the disclosure.

FIG. 7 schematically shows a non-limiting computing device 700 that can perform one or more of the above described methods and processes. For example, computing device 700 can represent a processor included in system 600 described above, and can be operatively coupled to, in communication with, or included in an OCT system or OCT image acquisition apparatus. Computing device 700 is shown in simplified form. It is to be understood that virtually any computer architecture can be used without departing from the scope of this disclosure. In different embodiments, computing device 700 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 700 includes a logic subsystem 702 and a data-holding subsystem 704. Computing device 700 can optionally include a display subsystem 706, a communication subsystem 708, an imaging subsystem 710, and/or other components not shown in FIG. 7. Computing device 700 can also optionally include user input devices such as manually actuated buttons, switches, keyboards, mice, game controllers, cameras, microphones, and/or touch screens, for example.

Logic subsystem 702 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 704 can include one or more physical, non-transitory, devices configured to hold data and/or instructions executable by the logic subsystem to implement the herein described methods and processes. When such methods and processes are implemented, the state of data-holding subsystem 704 can be transformed (e.g., to hold different data).

Data-holding subsystem 704 can include removable media and/or built-in devices. Data-holding subsystem 704 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 704 can include devices with one or more of the following characteristics: volatile, nonvolatile, dynamic, static, read/write, read-only, random access, sequential access, location addressable, file addressable, and content addressable. In some embodiments, logic subsystem 702 and data-holding subsystem 704 can be integrated into one or more common devices, such as an application specific integrated circuit or a system on a chip.

FIG. 7 also shows an aspect of the data-holding subsystem in the form of removable computer-readable storage media 712, which can be used to store and/or transfer data and/or instructions executable to implement the herein described methods and processes. Removable computer-readable storage media 712 can take the form of CDs, DVDs, HD-DVDs, Blu-Ray Discs, EEPROMs, flash memory cards, USB storage devices, and/or floppy disks, among others.

When included, display subsystem 706 can be used to present a visual representation of data held by data-holding subsystem 704. As the herein described methods and processes change the data held by the data-holding subsystem, and thus transform the state of the data-holding subsystem, the state of display subsystem 706 can likewise be transformed to visually represent changes in the underlying data. Display subsystem 706 can include one or more display devices utilizing virtually any type of technology. Such display devices can be combined with logic subsystem 702 and/or data-holding subsystem 704 in a shared enclosure, or such display devices can be peripheral display devices.

When included, communication subsystem 708 can be configured to communicatively couple computing device 700 with one or more other computing devices. Communication subsystem 708 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 700 to send and/or receive messages to and/or from other devices via a network such as the Internet.

When included, imaging subsystem 710 can be used acquire and/or process any suitable image data from various sensors or imaging devices in communication with computing device 700. For example, imaging subsystem 710 can be configured to acquire OCT image data, e.g., interferograms, as part of an OCT system, e.g., OCT system 602 described above. Imaging subsystem 710 can be combined with logic subsystem 702 and/or data-holding subsystem 704 in a shared enclosure, or such imaging subsystems can comprise periphery imaging devices. Data received from the imaging subsystem can be held by data-holding subsystem 704 and/or removable computer-readable storage media 712, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of identifying a choroidal neovascularization (CNV) region in an optical coherence tomography (OCT) angiogram comprising:

obtaining an inner retina angiogram and an outer retina angiogram that correspond to different regions of a retina;

subtracting the inner retina angiogram from the outer retina angiogram, thereby generating a subtracted outer retina angiogram;

generating a binary vascular mask from the subtracted outer retina angiogram; and multiplying the binary vascular mask by the outer retina angiogram, thereby identifying the CNV region in the outer retina angiogram.

2. The method of claim 1, further comprising calculating a CNV area of the CNV region.

3. The method of claim 1, wherein generating the binary vascular mask from the subtracted outer retina angiogram comprises:

generating a saliency map of CNV in the subtracted outer retina angiogram; and generating the binary vascular mask from the saliency map.

4. The method of claim 3, wherein the saliency map of CNV is generated using pattern recognition.

5. The method of claim 4, wherein the generation of a saliency map by pattern recognition comprises calculating a saliency model that incorporates brightness, orientation contrast, and positional distance as calculated by:

$$d_{orientation}(p_i, p_j) = \frac{1}{N}\sum d_{orientation}(p_i, p_j)\Big|_\theta$$

where $d_{orientation}(p_i,p_j)$ is the orientation contrast between patches $p_i$ and $p_j$ of the subtracted outer retinal angiogram, $d_{orientation}(p_i,p_j)|_\theta$ is a Euclidean distance between the patches $p_i$ and $p_j$ at a corresponding orientation $\theta$, $\theta=0°$, $45°$, $90°$, $135°$ and $N=4$, wherein $d_{orientation}(p_i,p_j)$ is normalized to the range [0,1]; and $$d(p_i, p_j) = \frac{d_{bright}(p_i, p_j) + d_{orientation}(p_i, p_j)}{2(1 + c \cdot d_{position}(p_i, p_j))}$$

wherein $d(p_i,p_j)$ is a distinctiveness between patches $p_i$ and $p_j$, $d_{position}(p_i,p_j)$ is a positional distance between patches $p_i$ and $p_j$, $d_{bright}(p_i,p_j)$ is Euclidean distance between summed intensities of the patches $p_i$ and $p_j$, normalized to the range [0,1], and c equals three.

6. The method of claim 5, further comprising performing multiscale enhancement of the saliency model by calculating saliency maps at multiple scales and combining the saliency maps at multiple scales.

7. The method of claim 5, further comprising modifying the saliency map to simulate context-awareness by:

identifying localized areas from the saliency map for which all pixels have a respective saliency value greater than a threshold; and redefining saliency values of pixels outside the localized areas according to a Euclidean distance of position to a closest pixel included in one of the localized areas.

8. The method of claim 3, wherein generating the vascular mask from the saliency map comprises applying a Laplacian edge detection filter to the saliency map, thereby generating an edge-enhanced saliency map.

9. The method of claim 8, wherein generating the edge-enhanced saliency map further comprises using a nonlinear filter to smooth the saliency map within a target region and preserve a boundary of the saliency map, thereby producing an edge-enhanced saliency map.

10. The method of claim 8, further comprising thresholding the edge-enhanced saliency map to extract a rough CNV region; and
applying morphological operators to the rough CNV region to remove small areas and fill holes, thereby generating the binary vascular mask.

11. The method of claim 10, wherein the thresholding includes using Otsu's method.

12. The method of claim 1, wherein the inner retinal angiogram is a two-dimensional (2D) en face inner retinal angiogram and the outer retinal angiogram is a 2D en face outer retinal angiogram.

13. The method of claim 12, further comprising
obtaining a set of cross-sectional OCT angiograms of the retina;
separating the set of cross sectional OCT angiograms into an inner set of cross-sectional angiograms and an outer set of cross-sectional angiograms based on one or more geographical markers;
projecting maximum flow values of the inner set of cross-sectional angiograms along an axial (Z) direction onto an X-Y plane, thereby generating the 2D en face inner retina angiogram; and
projecting maximum flow values along the axial (Z) direction of the outer set of cross-sectional angiograms onto the X-Y plane, thereby generating the 2D en face outer retina angiogram.

14. The method of claim 13, wherein the inner set of cross-sectional angiograms comprises flow values of the cross-sectional angiograms located between an internal limiting membrane and an outer plexiform layer, and wherein the outer set of cross-sectional angiograms comprises flow values of the cross-sectional angiograms located between the outer plexiform layer and Bruch's membrane.

15. The method of claim 1, further comprising applying a denoising filter to the inner retina angiogram prior to subtracting the inner retinal angiogram from the outer retinal angiogram.

16. The method of claim 1, wherein the denoising filter comprises a 20×20 pixel Gaussian filter or low pass filter.

17. A method of determining a choroidal neovascularization (CNV) area in an optical coherence tomography (OCT) angiogram comprising:
generating a saliency map of CNV from a two-dimensional (2D) en face outer retina angiogram using pattern recognition;
generating a binary vascular mask from the saliency map;
multiplying the binary vascular mask by the 2D en face outer retina angiogram, thereby identifying a CNV region in the outer retina angiogram; and
calculating the CNV area of the CNV region.

18. The method of claim 17, wherein the generation of a saliency map by pattern recognition comprises calculating a saliency model that incorporates brightness, orientation contrast, and positional distance as calculated by:

$$d_{orientation}(p_i, p_j) = \frac{1}{N}\sum d_{orientation}(p_i, p_j)\Big|_\theta$$

where $d_{orientation}(p_i,p_j)|_\theta$ is a Euclidean distance between patches $p_i$ and $p_j$ of the subtracted outer retinal angiogram at a corresponding orientation $\theta$, $\theta=0°, 45°, 90°, 135°$ and $N=4$, wherein $d_{orientation}(p_i,p_j)$ is normalized to the range $[0,1]$; and $$d(p_i, p_j) = \frac{d_{bright}(p_i, p_j) + d_{orientation}(p_i, p_j)}{2(1 + c \cdot d_{position}(p_i, p_j))}$$

wherein $d(p_i,p_j)$ is a distinctiveness between patches $p_i$ and $p_j$, $d_{position}(p_i,p_j)$ is a positional distance between patches $p_i$ and $p_j$, $d_{bright}(p_i,p_j)$ is Euclidean distance between summed intensities of the patches $p_i$ and $p_j$, normalized to the range $[0,1]$, and c equals three.

19. The method of claim 18, further comprising performing multiscale enhancement of the saliency model by calculating saliency maps at multiple scales and combining the saliency maps at multiple scales.

20. The method of claim 18, further comprising modifying the saliency map to simulate context-awareness by:
identifying localized areas from the saliency map for which all pixels have a respective saliency value greater than a threshold; and
redefining saliency values of pixels outside the localized areas according to a Euclidean distance of position to a closest pixel included in one of the localized areas.

21. The method of claim 17, further comprising
obtaining a 2D en face inner retina angiogram and the 2D en face outer retina angiogram that correspond to different regions of a retina; and
subtracting the 2D en face inner retina angiogram from the 2D en face outer retina angiogram prior to generating the saliency map from the outer retina angiogram.

22. The method of claim 21, further comprising
obtaining a set of cross-sectional OCT angiograms of the retina;
separating the set of cross sectional OCT angiograms into an inner set of cross-sectional angiograms and an outer set of cross-sectional angiograms based on one or more geographical markers;
projecting maximum flow values of the inner set of cross-sectional angiograms along an axial (Z) direction onto an X-Y plane, thereby generating the 2D en face inner retina angiogram; and
projecting maximum flow values along the axial (Z) direction of the outer set of cross-sectional angiograms onto the X-Y plane, thereby generating the 2D en face outer retina angiogram.

23. A system for determining a choroidal neovascularization (CNV) area in an optical coherence tomography (OCT) angiogram, the system comprising:
an OCT system configured to acquire an OCT dataset for a retina;
a logic subsystem; and
a data holding subsystem comprising machine-readable instructions stored thereon that are executable by the logic subsystem to:
obtain an inner retina angiogram and an outer retina angiogram from the OCT dataset, wherein the inner retina angiogram and the outer retina angiogram correspond to different regions of the retina;
subtract the inner retina angiogram from the outer retina angiogram to generate a subtracted outer retina angiogram;
generate a binary vascular mask from the subtracted outer retina angiogram; and apply the binary vascular mask to the outer retina angiogram to identify a CNV region in the outer retina angiogram; and calculate a CNV area of the CNV region.

24. The system of claim 23, wherein, to generate the binary vascular mask from the subtracted outer retina angiogram, the logic subsystem is to:

generate a saliency map of CNV in the subtracted outer retina angiogram; and generate the binary vascular mask from the saliency map.

25. The system of claim 24, wherein the saliency map of CNV is generated using pattern recognition.

26. The system of claim 25, wherein, to generate the saliency map by pattern recognition, the logic subsystem is to use a saliency model that incorporates brightness, orientation contrast, and positional distance as calculated by:

$$d_{orientation}(p_i, p_j) = \frac{1}{N} \sum d_{orientation}(p_i, p_j)\bigg|_\theta$$

where $d_{orientation}(p_i,p_j)$ is the orientation contrast between patches $p_i$ and $p_j$ of the subtracted outer retinal angiogram, $d_{orientation}(p_i,p_j)|_\theta$ is a Euclidean distance between the patches $p_i$ and $p_j$ at a corresponding orientation $\theta$, $\theta=0°, 45°, 90°, 135°$ and $N=4$, wherein $d_{orientation}(p_i,p_j)$ is normalized to the range [0,1]; and $$d(p_i, p_j) = \frac{d_{bright}(p_i, p_j) + d_{orientation}(p_i, p_j)}{2(1 + c \cdot d_{position}(p_i, p_j))}$$

wherein $d(p_i,p_j)$ is a distinctiveness between patches $p_i$ and $p_j$, $d_{position}(p_i,p_j)$ is a positional distance between patches $p_i$ and $p_j$, and $d_{bright}(p_i,p_j)$ is Euclidean distance between summed intensities of the patches $p_i$ and $p_j$, normalized to the range [0,1].

27. The system of claim 26, wherein the instructions are further to cause the logic subsystem to perform multiscale enhancement of the saliency model by calculating saliency maps at multiple scales and combining the saliency maps at multiple scales.

28. The system of claim 26, wherein the instructions are further to cause the logic subsystem to:

identify localized areas from the saliency map for which all pixels have a respective saliency value greater than a threshold; and redefine saliency values of pixels outside the localized areas according to a Euclidean distance of position to a closest pixel included in one of the localized areas.

29. The system of claim 23, wherein the inner retinal angiogram is a two-dimensional (2D) en face inner retinal angiogram and the outer retinal angiogram is a 2D en face outer retinal angiogram.

30. The system of claim 29, wherein, to obtain the 2D en face inner retinal angiogram and the 2D en face outer retinal angiogram, the logic subsystem is to:

obtain a set of cross-sectional OCT angiograms of the retina from the OCT dataset;

separate the set of cross sectional OCT angiograms into an inner set of cross-sectional angiograms and an outer set of cross-sectional angiograms based on one or more geographical markers;

project maximum flow values of the inner set of cross-sectional angiograms along an axial (Z) direction onto an X-Y plane to obtain the 2D en face inner retina angiogram; and project maximum flow values along the axial (Z) direction of the outer set of cross-sectional angiograms onto the X-Y plane to obtain the 2D en face outer retina angiogram.

31. The system of claim 30, wherein the inner set of cross-sectional angiograms comprises flow values of the cross-sectional angiograms located between an internal limiting membrane and an outer plexiform layer, and wherein the outer set of cross-sectional angiograms comprises flow values of the cross-sectional angiograms located between the outer plexiform layer and Bruch's membrane.

32. The system of claim 23, wherein the instructions are further to cause the logic subsystem to apply a denoising filter to the inner retina angiogram prior to subtraction of the inner retinal angiogram from the outer retinal angiogram.

* * * * *